United States Patent

Wade et al.

[11] 3,947,452
[45] Mar. 30, 1976

[54] 2-[(DIHYDROISOQUINOLINYL OR DIHYDROISOINDOL-2-YL)ALKYL]-1H-BENZ[DE]ISOQUINOLINE-1,3(2H)-DIONES

[75] Inventors: Peter C. Wade, Pennington, N.J.; Berthold Richard Vogt, Yardley, Pa.

[73] Assignee: E. R. Squibb & Sons, Inc., Princeton, N.J.

[22] Filed: Jan. 6, 1975

[21] Appl. No.: 538,976

[52] U.S. Cl............ 260/281 NH; 260/281 S; 424/258
[51] Int. Cl.$^2$............... C07D 401/06; C07D 217/24
[58] Field of Search................... 260/281 NH, 281 S

[56] References Cited
UNITED STATES PATENTS
3,330,834  7/1967  Senshu................................ 260/281
FOREIGN PATENTS OR APPLICATIONS
1,069,337  5/1967  United Kingdom................ 260/281

*Primary Examiner*—Alton D. Rollins
*Assistant Examiner*—Mark L. Berch
*Attorney, Agent, or Firm*—Lawrence S. Levinson; Merle J. Smith; Stephen B. Davis

[57] ABSTRACT

Compounds of the following formula and their acid addition salts

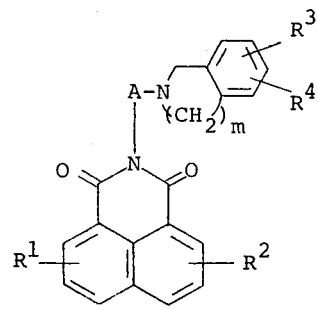

wherein $R^1$, $R^2$, $R^3$, and $R^4$ are independently selected from hydrogen, halogen, lower alkyl, lower alkoxy, lower alkylthio, nitro, cyano, amino and trifluoromethyl; A is a straight or branched chain alkylene of 1 to 8 carbons; and $m$ is 1 or 2 are disclosed. These compounds exhibit antidepressant and anti-anxiety activity. In addition these compounds are useful as anti-inflammatory agents.

17 Claims, No Drawings

2-[(DIHYDROISOQUINOLINYL OR DIHYDROISOINDOL-2-YL)ALKYL]-1H-BENZ-[DE]ISOQUINOLINE-1,3(2H)-DIONES

BACKGROUND OF THE INVENTION

Various naphthalimide compounds have been developed for use as dyes and optical brightening agents. Kimura et al., for example, at Chem. Abst., Vol. 62, 11950c, disclose N-[2-piperidinoethyl]-4-methoxy-1,8-naphthalimide (i.e. 6-methoxy-2-[2-(1-piperidinyl)ethyl]-1H-benz[de]isoquinoline-1,3(2H)-dione under the current Chem. Abst. nomenclature) as an optical brightening agent. Noguchi et al. in U.S. Pat. No. 3,625,947 disclose 2-[2-(2 or 4-pyridyl)ethyl]-1H-benz[de]isouqinoline-1,3(2H)-diones as fluorescent whitening agents.

Schenker et al. in U.S. Pat. No. 3,247,208 disclose that 1H-benz[de]isoquinoline-1,3(2H)-diones having a (1-substituted-4-piperidinyl) group in the 2-position possess anesthetic properties. Carron et al. in French Pat. No. 2,167,355 disclose that (4-phenyl)piperidine-2,6-diones having an alkylheteroalkyl substituent at the 1-position possess antidepressant activity. Imides having a nitroimidazolyethyl group as an N-substituent and possessing anti-bacterial and anti-protozoal activity are disclosed in U.S. Pat. Nos. 3,642,836 and 3,770,763 to Cusic et al. Certain imido dicarboxylic acid imides possessing various pharmacological properties are disclosed in U.S. Pat. No. 3,560,495 to Frankus et al.

SUMMARY OF THE INVENTION

This invention is directed to new 2-[(dihydroisoquinolinyl or dihydroisoindol-2-yl)alkyl]-1H-benz[de]isoquinoline-1,3(2H)-diones and their acid addition salts of the formula (I)

The symbols have the following meaning in formula I and throughout this specification.

$R^1$, $R^2$, $R^3$, and $R^4$ are each independently selected from hydrogen, halogen (preferably Br, Cl, or F), $CF_3$, lower alkyl, lower alkoxy, lower alkylthio, nitro, amino and cyano.

A is straight or branched chain alkylene of 1 to 8 carbons.

$m$ is 1 or 2.

DETAILED DESCRIPTION OF THE INVENTION

The various groups represented by the symbols have the meanings defined below and these definitions are retained throughout this specification.

The lower alkyl groups referred to throughout this specification include straight or branched chain hydrocarbon groups containing 1 to 4 carbons. Examples of the type of groups contemplated are methyl, ethyl, propyl, isopropyl, butyl, etc. The lower alkoxy groups include such lower alkyl groups attached to an oxygen, e.g., methoxy, ethoxy, propoxy, etc. The lower alkylthio groups include such lower alkyl groups attached to a sulfur, e.g., methylthio, ethylthio, etc.

Straight or branched chain alkylene of 1 to 8 carbons is intended to include groups such as $-(CH_2)_n-$ wherein $n$ is 1 to 8, $$-CH_2-CH-, \quad -CH_2-CH-(CH_2)_2-, \quad -CH_2-CH-CH-CH_2-,$$
$$\quad\quad |\quad\quad\quad\quad\quad\quad |\quad\quad\quad\quad\quad\quad\quad\quad |\quad\;\; |$$
$$\quad\;\; CH_3\quad\quad\quad\quad\quad\;\; C_2H_5\quad\quad\quad\quad\quad\;\; CH_3\; CH_3$$

etc.

Preferred embodiments of this invention are as follows:

$R^3$ is hydrogen, Cl, F, Br, $CH_3$ or $OCH_3$.

$R^4$ is hydrogen.

At least one of $R^1$ or $R^2$ is hydrogen and the other is hydrogen, Cl, F, Br, $CH_3$ or $OCH_3$.

A is straight or branched chain alkylene of 1 to 6 carbon atoms.

The most preferred compounds are:

$R^1$, $R^2$, $R^3$, and $R^4$ are hydrogen.

A is $-(CH_2)_n-$ wherein $n$ is an integer from 2 to 6.

The new compounds of this invention are prepared by the following reactions where A is straight or branched chain alkylene of 2 to 8 carbons.

The substituted naphthalic anhydride of formula II (II)

is reacted with an alkanolamine of formula III $$H_2N-A-OH \quad\quad\quad (III)$$

to yield the alcohol of formula IV (IV)

The alcohol of formula IV is converted to the intermediate of formula V (V)

where Y is a leaving group such as tosylate, methanesulfonate or halogen by treating the alcohol with p-toluenesulfonyl chloride, methanesulfonyl chloride, thionyl chloride, thionyl bromide or hydrogen iodide.

The intermediate of formula V is then converted to the final products of formula I by reactions with compounds of the formula VI (VI)

The substituted naphthalic anhydride of formula II can be converted directly to the final products of formula I by reacting the anhydride with compounds of formula VII

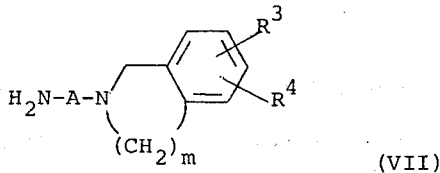

(VII)

The following schematic summarizes the reactions described above.

Also, the intermediate of formula V can be prepared by combining a substituted naphthalimide of formula VIII (VIII)

in an organic solvent with a polar organic solvent solution of a base, as for example an alcohol solution of potassium hydroxide, followed by the addition of a solution of the compound of formula IX, where A is straight or branched chain alkylene of 2 to 8 carbons $$Y'-A-Y \qquad \text{(IX)}$$

wherein Y' and Y are the same or different and are leaving groups selected from tosylate, methanesulfonate, or halogen and A is a straight or branched chain alkylene of 2 to 8 carbons.

Alternatively, the compounds of formula I wherein A is straight or branched alkylene of 2 to 8 carbons can be prepared by combining the anion of the substituted naphthalimide of formula VIII, described above, with a solution of the compound of formula X,

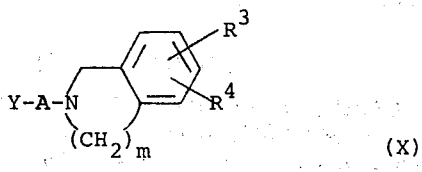

(X)

wherein Y is a leaving group as previously defined.

Compounds of formula I where A is —CH$_2$— are prepared by reacting the substituted naphthalimide of formula VIII suspended in a polar organic solvent such as dimethylformamide (DMF) with compounds of the formula VI and a source of formaldehyde such as aqueous formaldehyde or paraformaldehyde.

The various starting materials such as the substituted anhydrides of formula II and the alcohols of formula IV and the substituted naphthalimides of formula VIII are known in the art or are readily obtainable by known procedures. Further process details are also provided in the illustrative examples.

The compounds of formula I wherein any or all of R$^1$, R$^2$, R$^3$, and R$^4$ are amine are prepared by reducing the corresponding nitro substituted compound with a reducing agent such as hydrogen over a palladium catalyst or a suitable chemical reducing agent. This is preferably done as the last stage in the reaction procedures described above.

Depending on the reaction conditions and the starting materials used, the new compounds are obtained in the free form in the form of their acid addition salts. The salts thereof can be converted into the free compounds in a known manner such as by reaction with a basic agent. Free bases which may be obtained can be converted into pharmaceutically acceptable acid addition salts by reaction with a variety of acids. Acids useful for preparing these acid-addition salts include, inter alia, inorganic acids, such as the hydrohalic acids (e.g. hydrochloric and hydrobromic acid), sulfuric acid, nitric acid, and phosphoric acid, and organic acids such as maleic, fumaric, tartaric, citric, acetic, benzoic, 2-acetoxybenzoic, salicyclic, succinic, nicotinic, methanesulfonic or cyclohexanesulfamic.

The new compounds of the present invention including the acid addition salts are capable of modifying the central nervous system. When administered to mice, cats, rats, dogs, and other mammalian species in amounts ranging from about 0.5 mg. to about 100 mg. per kg. of body weight per day, these compounds in particular exhibit anti-depressant and anti-anxiety activity. A preferred dosage regimen for optimum results would be from about 1 mg. to about 5 mg. per kg. of body weight per day, and such dosage units are employed so that a total of from about 35 mg. to about 3 g. of active ingredient in single or divided doses are administered in a 24 hour period.

Compounds of formula I when administered to rats within the above stated preferred dosage range produced a significant anti-anxiety effect as demonstrated by increases in behavior which were formerly suppressed by punishment in a conflict test procedure [cf. J. R. Vogel, B. Beer, D. Clody, Psychopharmacologist, 21, 1 (1970)].

The antidepressant activity of the compounds of formula I is demonstrated by their ability to antagonize tetrabenazine-induced ptosis according to the procedure of Vernier et al. ("The Pharmacodynamics of Amitriptyline", *Psychosomatic Medicine*, (1962), pages 683–690) and also by their ability to block the reuptake of monoamines in vitro according to the procedure of Horn et al. (*Molecular Pharmacology*, 7th Ed., (1971), page 66).

The compounds of formula I are also useful as anti-inflammatory agents and may be used, for example, in a manner similar to phenylbutazone or indomethacin. They may be used to decrease joint swelling, tenderness, pain and stiffness in mammalian species, e.g., in conditions such as rheumatoid arthritis. The quantity administered ranges from about 1 mg. to about 15 mg. per kg. of body weight per day.

For any of these pharmaceutical purposes a compound or mixture of compounds of formula I or their pharmaceutically acceptable acid addition salts may be administered orally or parenterally in a conventional dosage form such as tablet, capsule, injectable or the like. These may be conventionally formulated in an oral or parenteral dosage form by compounding with a conventional vehicle, excipient, binder, preservative, stabilizer, flavor or the like as called for by accepted pharmaceutical practice.

The following examples are illustrative of the invention and represent preferred embodiments. Other modifications may be readily produced by suitable variations of the reactions. All temperatures are on the centigrade scale.

EXAMPLE 1

2-[2-(3,4-Dihydro-2(1H)-isoquinolinyl)ethyl]-1H-benz[de]-isoquinoline-1,3(2H)-dione, hydrochloride (1:1)

a.

2-(2-Hydroxyethyl)-1H-benz[de]isoquinoline-1,3(2H)-dione 50 g. (0.252 mole) of naphthalic anhydride and 16 g. (0.262 mole) of ethanolamine are refluxed for three hours in 200 ml. of water (the solution is never complete). After cooling to 25° the water is decanted off and the residue recrystallized from 95% ethanol to yield 47.8 g. of 2-(2-hydroxyethyl)-1H-benz[de]isoquinoline-1,3(2H)-dione; m.p. 172°–173°.

b.

2-(2-Hydroxyethyl)-1H-benz[de]isoquinoline-1,3(2H)-dione, 4-methylbenzenesulfonate ester 52 g. (0.216 mole) of the 2-(2-hydroxyethyl)-1H-benz[de]isoquinoline-1,3(2H)-dione and 100 g. (0.525 mole) of p-toluenesulfonyl chloride are added to 600 ml. of pyridine previously cooled to 5°. The mixture is shaken briefly then allowed to stand overnight at 5°. The mixture is then poured into 3000 ml. of ice and water, stirred for 15 minutes and filtered. The insoluble material is stirred with fresh water, filtered off again and dried overnight at 25° (0.1 mm.) yielding 83 g. of 2-(2-hydroxyethyl)-1H-benz[de]isoquinoline-1,3(2H)-dione, 4-methylbenzenesulfonate ester.

c.

2-[2-(3,4-Dihydro-2(1H)-isoquinolinyl)ethyl]-1H-benz[de]-isoquinoline-1,3(2H)-dione, hydrochloride (1:1)

10.3 g. (0.025 mole) of the ester from part (b) and 7.6 g. (0.05 mole) of 1,2,3,4-tetrahydroisoquinoline are refluxed in 300 ml. of toluene for one hour. The mixture is then cooled to 25° for three hours and the resulting precipitate is removed by filtration. The filtrate is shaken with excess 10% aqueous HCl producing a gum which is insoluble in both layers. After several minutes the gum crystallizes and is filtered from the two liquid phases. Recrystallization from absolute ethanol and drying at 80° (0.1 mm.) for ten hours yields 5 g. of 2-[2-(3,4-dihydro-2(1H)-isoquinolinyl)ethyl]-1H-benz[de]isoquinoline-1,3(2H)-dione, hydrochloride (1:1); m.p. 259°–261° (dec.).

EXAMPLES 2–12

Following the procedure of example 1 but substituting the alkanolamine shown in Col. I for the ethanolamine the following products are obtained wherein A is the radical shown in Col. II.

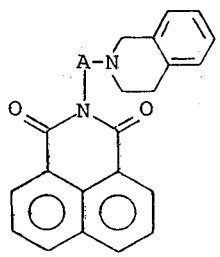

| Ex. | Col. I | Col. II |
|---|---|---|
| 2 | $H_2N-(CH_2)_3-OH$ | $-(CH_2)_3-$ |
| 3 | $H_2N-(CH_2)_4-OH$ | $-(CH_2)_4-$ |
| 4 | $H_2N-(CH_2)_5-OH$ | $-(CH_2)_5-$ |
| 5 | $H_2N-(CH_2)_6-OH$ | $-(CH_2)_6-$ |
| 6 | $H_2N-(CH_2)_7-OH$ | $-(CH_2)_7-$ |
| 7 | $H_2N-(CH_2)_8-OH$ | $-(CH_2)_8-$ |
| 8 | $H_2N-CH_2-CH(CH_3)-CH_2-OH$ | $-CH_2-CH(CH_3)-CH_2-$ |
| 9 | $H_2N-CH(CH_3)-(CH_2)_3-OH$ | $-CH(CH_3)-(CH_2)_3-$ |
| 10 | $H_2N-(CH_2)_3-CH(CH_3)-OH$ | $-(CH_2)_3-CH(CH_3)-$ |
| 11 | $H_2N-CH_2-CH(C_3H_7)-(CH_2)_2-OH$ | $-CH_2-CH(C_3H_7)-(CH_2)_2-$ |
| 12 | $H_2N-CH(CH_3)-CH_2-CH(CH_3)-OH$ | $-CH(CH_3)-CH_2-CH(CH_3)-$ |

EXAMPLE 13

2-[2-(1,3-Dihydro-2H-isoindol-2-yl)ethyl]-1H-benz[de]isoquinoline-1,3(2H)-dione, hydrochloride Following the procedure of example 1 but substituting an equimolar amount of 2,3-dihydro-1H-isoindole for the 1,2,3,4-tetrahydroisoquinoline in part (c), one obtains 2-[2-(1,3-dihydro-2H-isoindol-2-yl)ethyl]-1H-benz[de]isoquinoline-1,3(2H)-dione, hydrochloride.

Similarly by employing the alkanolamines of examples 2 to 12 in the above procedure other compounds within the scope of the invention are prepared.

EXAMPLES 14–38

Following the procedure of example 1 but substituting for the 1,2,3,4-tetrahydroisoquinoline in part (c) the compounds shown below in Col. I one obtains the products shown in Col. II.

Col. I

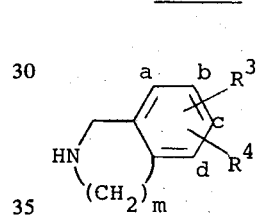

Col. II

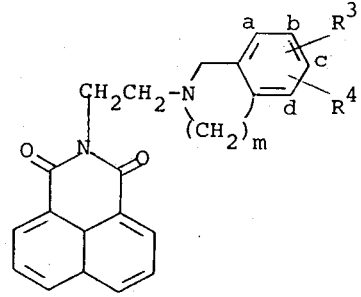

| Ex. | m | R³ and R⁴ | | | |
|---|---|---|---|---|---|
| | | a | b | c | d |
| 14 | 2 | H | $CH_3$ | H | H |
| 15 | 1 | H | H | $CH_3$ | H |
| 16 | 2 | H | H | H | $C_2H_5$ |
| 17 | 2 | CN | H | H | H |
| 18 | 1 | H | CN | H | H |
| 19 | 2 | $OCH_3$ | H | H | H |
| 20 | 1 | H | H | $OC_3H_7$ | H |
| 21 | 2 | H | Cl | H | H |
| 22 | 2 | Cl | H | H | H |
| 23 | 1 | H | H | Cl | H |
| 24 | 1 | H | Br | H | H |
| 25 | 2 | H | H | F | H |
| 26 | 2 | H | $NO_2$ | H | H |
| 27 | 1 | H | H | $NO_2$ | H |
| 28 | 2 | H | $CF_3$ | H | H |
| 29 | 1 | H | H | $CF_3$ | H |
| 30 | 2 | H | $NH_2$ | H | H |
| 31 | 1 | H | H | $NH_2$ | H |
| 32 | 2 | $SC_3H_7$ | H | H | H |
| 33 | 1 | H | $SCH_3$ | H | H |
| 34 | 2 | H | Cl | H | Cl |
| 35 | 1 | H | Br | H | Br |
| 36 | 2 | Cl | H | H | Cl |
| 37 | 2 | H | $OCH_3$ | $OCH_3$ | H |
| 38 | 1 | H | H | Cl | $CF_3$ |

EXAMPLE 39

2-[4-(3,4-Dihydro-2(1H)-isoquinolinyl)butyl-1H-benz[de]-isoquinoline-1,3(2H)-dione, hydrochloride (1:1)

a.

2-(4-Bromobutyl)-1H-benz[de]isoquinoline-1,3(2H)-dione 100 g. (0.5 mole) of 1,8-naphthalimide is suspended in 2100 ml. of dimethylformamide and the mixture is heated to 90° to form a complete solution. A solution of 36.3 g. (0.55 mole) of potassium hydroxide (85%) in 100 ml. of methanol is added resulting in the immediate formation of a yellow precipitate. The resulting mixture is stirred for one hour at 90° and cooled to 25°. 245 g. (1.0 mole) of 1,4-dibromobutane is added and the mixture is again heated to 90° and stirred for an additional hour. A precipitate remains in the mixture but is more granular than the initial material. The reaction mixture is cooled and the precipitate filtered off. The solvent is removed under vacuum and the residue is diluted with 500 ml. of hexane immediately precipitating crude 2-(4-bromobutyl)-1H-benz[de]isoquinoline-1,3(2H)-dione. The precipitate is filtered off, washed with fresh hexane and dried for 2 hours at 50° (0.1 mm.) to yield 2-(4-bromobutyl)-1H-benz[de]isoquinoline-1,3(2H)-dione. An analytically pure sample is prepared by dissolving the above product in hot 95% ethanol and recrystallizing by allowing the solution to cool to 25°. The resulting precipitate is dried for two hours at 50° (0.1 mm.) to yield pure 2-(4-bromobutyl-1H-benz[de]isoquinoline-1,3(2H)-dione, m.p. 113°–115°.

b.

2-[4-(3,4-Dihydro-2(1H)-isoquinolinyl)butyl]-1H-benz[de]-isoquinoline-1,3(2H)-dione; hydrochloride (1:1)

10 g. (0.03 mole) of 2-(4-bromobutyl)-1H-benz[de]isoquinoline-1,3(2H)-dione from part (a), 4.4 g. of (0.033 mole) of 1,2,3,4-tetrahydroisoquinoline, and 15 g. of sodium carbonate are combined in 200 ml. of toluene and refluxed for 24 hours. After cooling to 25°, 100 ml. of water is added and the resulting mixture is shaken. Some insoluble gum is filtered off and the two layers of the filtrate are separated. The organic layer is washed with water and shaken with excess 10% aqueous HCl. The oil that separates from both layers crystallizes after several hours. This material is partitioned between 10% NaOH chloroform. The chloroform layer is dried ($Na_2SO_4$) and the solvent removed under vacuum. The residue is crystallized from 95% ethanol to yield 8.4 g. of 2-[4-(3,4-dihydro-2(1H)-isoquinolinyl)-butyl]-1H-benz[de]isoquinoline-1,3(2H)-dione; m.p. 113°–115°.

The free base is dissolved in 200 ml. of warm absolute ethanol and treated with a 10% excess of ethereal.HCl. After two hours at 5°, the resulting precipitate is filtered off and dried at 70° (0.1 mm.) for three hours to yield 8.5 g. of 2-[4-(3,4-dihydro-2(1H)-isoquinolinyl)butyl]-1H-benz[de]isoquinoline-1,3(2H)-dione, hydrochloride (1:1); m.p. 263°–266°.

EXAMPLE 40

2-[5-(3,4-Dihydro-2(1H)-isoquinolinyl)pentyl]-1H-benz[de]-isoquinoline-1,3(2H)-dione, hydrochloride (1:1)

a.

2-(5-Bromopentyl)-1H-benz[de]isoquinoline-1,3(2H)-dione

Following the procedure of part (a) of example 39 but substituting 1,5-dibromopentane for the 1,4-dibromobutane, one obtains 2-(5-bromopentyl)-1H-benz[de]isoquinoline-1,3(2H)-dione; m.p. 113°–115°.

b.

2-[5-(3,4-Dihydro-2(1H)-isoquinolinyl)pentyl]-1H-benz[de]-isoquinoline-1,3(2H)-dione, hydrochloride (1:1)

Following the procedure of part (b) of example 39 but substituting 2-(5-bromopentyl)-1H-benz[de]isoquinoline-1,3(2H)-dione for the 2-(4-bromobutyl)-1H-benz[de]isoquinoline-1,3(2H)-dione, one obtains 2-[5-(3,4-dihydro)-2(1H)-isoquinolinyl)-pentyl]-1H-benz[de]isoquinoline-1,3(2H)-dione, hydrochloride (1:1).

EXAMPLE 41

2-[6-(3,4-Dihydro)-2(1H)-isoquinolinyl)hexyl]-1H-benz[de]-isoquinoline-1,3(2H)-dione, hydrochloride (1:1)

a.

2-(6-Bromohexyl)-1H-benz[de]isoquinoline-1,3(2H)-dione

Following the procedure of part (a) of example 39 but substituting 1,6-dibromohexane for the 1,4-dibromobutane, one obtains 2-(6-bromohexyl)-1H-benz[de]isoquinoline-1,3(2H)-dione; m.p. 95°–96°.

b.

2-[6-(3,4-Dihydro)-2(1H)-isoquinolinyl)hexyl]-1H-benz[de]-isoquinoline-1,3(2H)-dione, hydrochloride (1:1)

Following the procedure of part (b) of example 39 but substituting 2-(6-bromohexyl)-1H-benz[de]isoquinoline-1,3(2H)-dione for the 2-(4-bromobutyl)-1H-benz[de]isoquinoline-1,3-(2H)-dione, one obtains 2-[6-(3,4-dihydro-2(1H)-isoquinolinyl)-hexyl]-1H-benz[de]isoquinoline-1,3(2H)-dione, hydrochloride (1:1).

Alternatively, the procedure of examples 39–41 can be employed to prepare the compounds of examples 1–38.

EXAMPLE 42

2-[(3,4-Dihydro-2(1H)-isoquinolinyl)methyl]-1H-benz[de]isoquinoline-1,3(2H)-dione An equimolar mixture of 1,2,3,4-tetrahydroisoquinoline, aqueous formaldehyde, and 1,8-naphthalimide is suspended in a small amount of dimethylformamide and the mixture is heated until dissolution is complete. The solution is allowed to stand at room temperature and the resulting precipitate is filtered off and dried to yield 2-[(3,4-dihydro-2(1H)-isoquinolinylmethyl]-1H-benz[de]isoquinoline-1,3(2H)-dione.

Similarly, by substituting for the 1,2,3,4-tetrahydroisoquinoline in the above procedure the 2,3-dihydro-1H-isoindole from example 13 or the compounds from Col. I of examples 14 to 38, other compounds within the scope of the invention are obtained.

EXAMPLES 43–68

Following the procedure of example 1 but substituting for the 2-(2-hydroxyethyl)-1H-benz[de]isoquinoline-1,3(2H)-dione, 4-methylbenzenesulfonate ester the ester shown in Col. I one obtains the product shown in Col. II.

Col. I
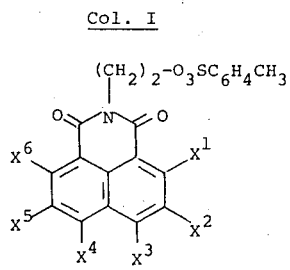

Col. II
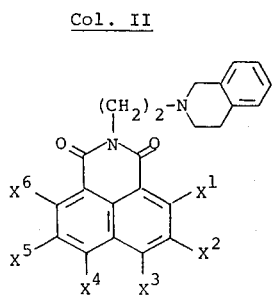

| Ex. | $X^1$ | $X^2$ | $X^3$ | $X^4$ | $X^5$ | $X^6$ |
|---|---|---|---|---|---|---|
| 43 | H | H | Br | H | H | H |
| 44 | H | Cl | H | H | H | H |
| 45 | H | Br | H | H | H | H |
| 46 | H | F | H | H | H | H |
| 47 | H | I | H | H | H | H |
| 48 | H | Cl | H | H | Cl | H |
| 49 | Br | H | H | H | H | H |
| 50 | H | H | Cl | Cl | H | H |
| 51 | H | H | $CH_3$ | H | H | H |
| 52 | H | H | $C_2H_5$ | H | H | H |
| 53 | H | H | i-$C_3H_7$ | H | H | H |
| 54 | H | H | $CH_3$ | $CH_3$ | H | H |
| 55 | H | H | $OCH_3$ | H | H | H |
| 56 | H | H | $OC_2H_5$ | H | H | H |
| 57 | H | H | $OC_3H_7$ | H | H | H |
| 58 | H | H | $OCH_3$ | $OCH_3$ | H | H |
| 59 | H | $NO_2$ | H | H | H | H |
| 60 | H | H | $NO_2$ | H | H | H |
| 61 | H | $CF_3$ | H | H | H | H |
| 62 | H | H | $CF_3$ | H | H | H |
| 63 | H | CN | H | H | H | H |
| 64 | H | H | CN | H | H | H |
| 65 | H | H | $NH_2$ | H | H | H |
| 66 | H | $NH_2$ | H | H | H | H |
| 67 | H | $SC_3H_7$ | H | H | H | H |
| 68 | H | H | $SCH_3$ | H | H | H |

Similarly, by employing the ester of Col. I of examples 43–68 in the procedure of Example 13 to 38, other compounds within the scope of this invention are prepared.

Similarly, by following the procedure of examples 2–12, but employing a substituted 1,8-naphthalic anhydride of formula II wherein the substituents are those listed under the headings $X^1$, $X^2$, $X^3$, $X^4$, $X^5$, and $X^6$ in examples 43–68, other compounds within the scope of the invention are prepared. Also, by following the procedures of example 39 or 42 but employing a substituted 1,8-naphthalimide of formula VIII wherein the substituents are those listed under the headings $X^1$, $X^2$, $X^3$, $X^4$, $X^5$, and $X^6$ in examples 43 to 68, other compounds within the scope of this invention are prepared.

What is claimed is:

1. A compound of the formula:

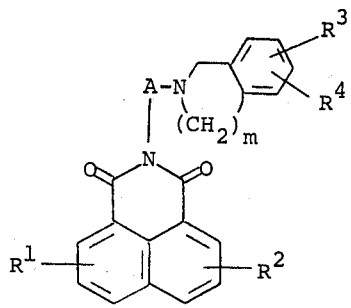

wherein $R^1$, $R^2$, $R^3$, and $R^4$ are each independently selected from the group consisting of hydrogen, halogen, lower alkyl of 1 to 4 carabons, lower alkoxy of 1 to 4 carbons, lower alkylthio of 1 to 4 carbons, nitro, cyano, amino, and trifluoromethyl; A is a straight or branched chain alkylene of 1 to 8 carbons; and $m$ is 1 or 2; and a pharmaceutically acceptable acid addition salt therof.

2. The compound of claim 1 wherein at least one of $R^1$ and $R^2$ is hydrogen and the other is selected from the group consisting of hydrogen, Cl, Br, F, methyl and methoxy; $R^3$ is selected from the group consisting of hydrogen, Cl, Br, F, methyl, and methoxy; $R^4$ is hydrogen; A is a straight or branched chain alkylene of 1 to 6 carbons; and $m$ is 2.

3. The compound of claim 2 wherein $R^1$, $R^2$, and $R^3$ are hydrogen; and A is a straight chain alkylene of 2 to 6 carbons.

4. The compound of claim 3 wherein A is —$(CH_2)_2$—.

5. The compound of claim 4 having the name 2-[2-(3,4-dihydro-2(1H)-isoquinolinyl)ethyl]-1H-benz[de]isoquinoline-1,3(2H)-dione, hydrochloride (1:1).

6. The compound of claim 3 wherein A is —$(CH_2)_3$—.

7. The compound of claim 3 wherein A is —$(CH_2)_4$—.

8. The compound of claim 7 having the name 2-[4-(3,4-dihydro-2(1H)-isoquinolinyl)butyl]-1H-benz[de]isoquinoline-1,3-(2H)-dione, hydrochloride (1:1).

9. The compound of claim 3 wherein A is —$(CH_2)_5$—.

10. The compound of claim 3 wherein A is —$(CH_2)_6$—.

11. The compound of claim 1 wherein at least one of $R^1$ and $R^2$ is hydrogen and the other is selected from the group consisting of hydrogen, Cl, Br, F, methyl and methoxy; $R^3$ is selected from the group consisting of hydrogen, Cl, Br, F, methyl and methoxy; $R^4$ is hydrogen; A is a straight or branched chain alkylene of 1 to 6 carbons; and $m$ is 1.

12. The compound of claim 11 wherein $R^1$, $R^2$ and $R^3$ are hydrogen; and A is a straight chain alkylene of 2 to 6 carbons.

13. The compound of claim 12 wherein A is —$(CH_2)_2$—.

14. The compound of claim 12 wherein A is —$(CH_2)_3$—.

15. The compound of claim 12 wherein A is —$(CH_2)_4$—.

16. The compound of claim 12 wherein A is —$(CH_2)_5$—.

17. The compound of claim 12 wherein A is —$(CH_2)_6$—.

* * * * *

UNITED STATES PATENT AND TRADEMARK OFFICE
CERTIFICATE OF CORRECTION

PATENT NO. : 3,947,452
DATED : March 30, 1976
INVENTOR(S) : Peter C. Wade et al.

It is certified that error appears in the above-identified patent and that said Letters Patent are hereby corrected as shown below:

Example 12, Col. II, "$-\underset{\underset{CH_3}{|}}{\overset{\|}{C}}H-CH_2-\underset{\underset{CH_3}{|}}{C}H-$" should read -- $-\underset{\underset{CH_3}{|}}{C}H-CH_2-\underset{\underset{CH_3}{|}}{C}H-$ Col. 12, line 15, "carabons" should read --carbons--.

Signed and Sealed this fifteenth Day of June 1976

[SEAL]

Attest:

RUTH C. MASON
*Attesting Officer*

C. MARSHALL DANN
*Commissioner of Patents and Trademarks*